United States Patent
Petersen et al.

(10) Patent No.: US 8,195,478 B2
(45) Date of Patent: Jun. 5, 2012

(54) NETWORK PERFORMANCE MONITOR

(75) Inventors: Eric G. Petersen, Aloha, OR (US);
Steven D. Baker, Beaverton, OR (US);
Steven J. Marcaccini, Aurora, OR (US);
Mark A. Heritage, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1001 days.

(21) Appl. No.: 11/683,252

(22) Filed: Mar. 7, 2007

(65) Prior Publication Data

US 2008/0221918 A1    Sep. 11, 2008

(51) Int. Cl.
*G06Q 10/00* (2012.01)
*G06Q 50/00* (2012.01)
*H04Q 11/00* (2006.01)

(52) U.S. Cl. .......................................... 705/2; 370/245
(58) Field of Classification Search ............. 705/2, 3; 370/241, 245
See application file for complete search history.

(56) References Cited

U.S. PATENT DOCUMENTS

| | | | |
|---|---|---|---|
| 6,757,543 B2 * | 6/2004 | Moran et al. | 455/456.1 |
| 6,885,641 B1 * | 4/2005 | Chan et al. | 370/252 |
| 6,937,150 B2 * | 8/2005 | Medema et al. | 340/539.12 |
| 7,099,942 B1 * | 8/2006 | Wilson et al. | 709/224 |
| 2004/0095237 A1 | 5/2004 | Chen et al. | |
| 2005/0094567 A1 * | 5/2005 | Kannan et al. | 370/241 |
| 2005/0174947 A1 * | 8/2005 | Beck et al. | 370/241 |
| 2006/0049936 A1 * | 3/2006 | Collins et al. | 340/539.11 |
| 2006/0069956 A1 * | 3/2006 | Steinberg et al. | 714/25 |
| 2006/0155584 A1 | 7/2006 | Aggarwal | |

FOREIGN PATENT DOCUMENTS

| | | |
|---|---|---|
| KR | 101999014636 A | 2/1999 |
| KR | 1020030046903 A | 6/2003 |

OTHER PUBLICATIONS

International Search Report/Written Opinion (ISR/WO), Jul. 22, 2008, 6 pages.
Cisco, Cisco Network Application Performance Analysis (NAPA) Solution, Downloaded from internet on Jun. 6, 2007. (3 pages).
S.D. Baker, et al. Performance Measure of ISM-BAND and Conventional Telemetry, IEEE EMBS, vol. 23, pp. 27-36, May/Jun. 2004. (11 pages).

* cited by examiner

*Primary Examiner* — Gerald J. O'Connor
*Assistant Examiner* — Neha Patel
(74) *Attorney, Agent, or Firm* — Hiscock & Barclay, LLP

(57) ABSTRACT

Disclosed in this specification is a method for monitoring a network, such as the central monitoring station of a medical facility. Performance data from each of the network components of interest is monitored for compliance with certain component-specific criteria. Responses are generated if the performance data satisfies, or fails to satisfy, such criteria.

15 Claims, 10 Drawing Sheets

NETWORK PERFORMANCE MONITOR

FIELD OF THE INVENTION

This invention relates generally to mission critical data delivery on shared networks, and more particularly, to life-critical delivery of patient information to a central monitor and to clinicians across 802.3 Local Area Networks (LANs) and 802.11 Wireless LANs.

BACKGROUND OF THE INVENTION

Vintage analog medical telemetry from the 1970s exhibited a typical maximum data loss of 50 minutes per day—an enormous improvement over no patient monitoring. The initial digital systems stumbled as they exhibited 75 minutes per day of lost data. Over time improvements were made, but second generation Ultra High Frequency (UHF) telemetry, including most systems running in the Wireless Medical Telemetry Service (WMTS) still exhibited 25 minutes of dropout per day.

The medical world received a wakeup call when a High Definition Television (HDTV) station test near the Baylor Hospital impacted patient telemetry. If a digital television station transmits in the same channel as UHF telemetry, virtually no data are transmitted successfully, which is why the Food and Drug Administration (FDA) and Association for the Advancement of Medical Instrumentation (AAMI) petitioned the Federal Communications Commission (FCC) for a band dedicated to medical telemetry, resulting in the Wireless Medical Telemetry Service (WMTS). This allocation precludes a television station using the dedicated band, but does not result in any improvement over the 25 minutes/day of dropout Some companies have improved on second generation digital telemetry systems by copying the 802.11 Access Point (AP) concept, including using spread spectrum technology. With any spread spectrum technology, the high ratio of available bandwidth to data bandwidth is important, but the widest band of the WMTS spans only 6 MHz. As a result, spread spectrum systems that use this band render useless nearby second generation systems also in this band. Other Wireless Medical Telemetry Service solutions include re-crystalling existing systems. While this expensive "upgrade" removes the worry of an in-band HDTV station, it does nothing to improve the 25 minutes per day of dropout. Philips uses the yet-smaller 1.4 GHz band of the WMTS with channels limited to only 12,500 bps at a range of 30 feet.

About the same time as Wireless Medical Telemetry Service was being considered in 1999, IEEE 802.11 standard was ratified. Some medical companies embraced the concept of standards-based solutions as a means to make better use of networks by sharing one network among many applications. At that time, the promise was unrealized because standards and protocols for security and quality of service had not yet been developed. What 802.11 brought was a 10-fold decrease in dropout [S. D. Baker, et al., "Performance Measure of ISM-Band and Conventional Telemetry," *IEEE EMBS*, vol. 23, pp. 27-36, May/June 2004] that is realized because of a robust modulation, intelligent communication protocols, and good radio frequency network design.

Since then, wireless Local Area Networks (LANs) have become ubiquitous in many industries and even within the cautious healthcare environment: nearly 50 percent of hospitals have 802.11 LANs installed and over 80 percent are planning to have an 802.11 networks deployed to support Electronic Medical Records (EMR) within the next two years.

Market forces, including demand for toll-quality wireless Voice over Internet Protocol (VoIP) and secure communication, resulted in supplementary standards that allow multiple applications to securely (802.11i) share an Access Point with protection for critical data transactions (802.11e). Thin Access Point architectures allow information technology staff to manage the entire wireless network from a single point. Chipsets supporting the 802.11a physical layer have been available for several years and infrastructures are now typically installed with 802.11a/g support. In fact enterprise-class solutions are only available with 802.11 a/b/g chipsets (Concurrent with the rise of 802.11 a/b/g chipsets came the last of 802.11b-only radios. Some institutions now ban 802.11b and use 802.11g or 802.11a/g only.). In the United States, the FCC recently augmented the 802.11a band with an additional 255 MHz of bandwidth resulting in a total of 555 MHz, for a total of 21 non-overlapping channels. This is more than all bandwidth allocated for broadcast television, AM and FM radio, Cellular, and Personal Communications Service (PCS) combined. Just as One megawatt Effective Isotropic Radiate Power (EIRP=transmit power*antenna gain) TV stations spaced hundreds of miles apart can re-use each TV channel, 200 milliwatt EIRP 802.11 Access Points spaced hundreds of feet apart can also re-use each 802.11 channels. The 802.11a APs' EIRP is 5 million times smaller than that of TV stations. Because channels of this power difference, the 802.11 channel re-use is measured in tens of meters and APs channels can be re-used every 150 feet or so. This results in a bandwidth only limited by the size of the hospital and the speed of the information technology backbone.

Many hospitals have already identified multiple applications that can share a single 802.11 network. Some hospitals justify the cost of an enterprise-wide 802.11a/g network upgrade simply to meet the Joint Commission on Accreditation of Healthcare Organizations (JCAHO) requirements for Bar Code Medical Administration (BCMA) where a patient's identification and medications are scanned prior to administration, with the data verified by a server on the other side of a wireless LAN.

Table 1 shows some of the network-communication applications in use in hospitals and a summary of what wireless solutions exist to support these applications on an enterprise scale. Note that 802.11g can be used without much issue at the unit or department level, but with only three non-overlapping channels, it is not well suited for enterprise installations because of the difficulty in laying out a network without neighboring APs sharing, and therefore interfering on the same channel. If one attempts to have redundant coverage, where multiple APs provide RF coverage of the same area, then 802.11b/g is not suitable. Still the concepts embodied in this patent pertain to both 802.11g and 802.11b networks.

TABLE 1

Wireless Solutions and Applications

| | 802.11a | 802.11g[1] | Cellular | Paging | PLMR | WMTS | MICS | Bluetooth |
|---|---|---|---|---|---|---|---|---|
| Nurse Call | • | • | | • | | | | |
| Voice | • | • | • | | •[2] | | | •[3] |
| Telemetry Bedside | • | • | | | | • | • | |
| Patient Monitoring | • | • | | | | • | • | |
| Clinician Alarm Notification | • | • | | • | | | | |
| BCMA | • | • | | | | | | |
| Remote Access | • | • | • | | | | | |
| Guest Access | • | • | | | | | | |
| EMR/CIS Applications | • | • | | | | | | |
| Streaming Video[4] | • | • | | | | | | |
| E-mail | • | • | • | | | | | |
| Location | • | • | •[5] | | | | | |
| Cart on Wheels | • | • | | | | | | |
| Backup Communication | •[6] | • | | | •[2] | | | |
| Implanted Device | | | | | | | • | |
| Patient Billing Supports | • | • | | | | | | |
| Redundant Coverage | • | | | • | • | • | | |
| Geographic Scale | Enterprise/ Campus | Unit/ Floor | World | World | Unit/ Floor | Unit/ Floor | Room | Room |

[1]802.11 b/g solutions work on a limited scale, e.g., for a single hospital unit with minimal traffic, due to the limited number of 3 non-overlapping channels.
[2]Since PLMR does not use a network, it is a good emergency backup, but communication across the enterprise is not guaranteed. Private calls are not supported.
[3]Headset to earpiece only
[4]VGA resolution at 30 frames per second or better
[5]Outdoor location only - indoor GPS service is not dependable because S-Band doesn't penetrate through floors and walls well.
[6]With redundant installation and backup power installed The primary advantage and rationale for these technologies being deployed in the healthcare enterprise is due to the technologies being highly mobile. Healthcare facilities are one of the most communications intensive environments that exist today. Many devices already in use including laptop computers, personal digital assistants (PDAs), cellular phones, infusion pumps, and patient monitors now come with embedded 802.11 radios. Moving forward, we see that one cost effective way for improving work flow, productivity, and patient outcomes will involve using tools such as Wireless VoIP, PDAs supporting applications such as drug formularies, nurse-call, and patient-clinician alarm notification, and Patient monitoring on an enterprise-wide network that has been designed for the intended use. Without this, patients are at increased risk for not being continuously monitored, and clinician's frustration with not being able to use the wireless services for their clinical needs will continue to increase. Clinicians should be able to access and update patient records including medications at the bedside, rather than going out into the hall where the Cart on Wheels (CoW) has wireless access or even back to the nurse's station. Wireless VoIP, which can be used for paging, as a walkie-talkie, or as a phone to dial long distance requires a higher radio frequency coverage level than is required for downloading e-mail.

Hospitals are a challenging radio frequency (RF) environment with shielded rooms, significant amounts of RF-reflective metal (food carts that interrupted conventional telemetry), and a high availability requirement for all applications. Because of this, a routine wireless installation to simply provide RF coverage appropriate for an office environment is not acceptable. As an example, some early adopter hospitals and wireless installers designed and installed to specifications simply to provide minimum RF coverage, even if this meant occasional dropped packets. Others opted for coverage where clinicians are most of the time. The assumption behind these installations may have been that wireless users would seek out good connectivity locations and these early adopters did not need support for "RF-everywhere" applications such as VoIP. While some people view any and all wireless LAN installations identically, it is not reasonable to ascribe this philosophy to a network that supports life critical applications. Medical device networks intended to support life critical applications, such as physiologic alarms, must use highly reliable networks that result from the verification and validation prescribed by the FDA. A network that simply provides RF coverage most of the time in most areas of the hospital is not acceptable. Proper requirements specification and design is required for the network to reliably support multiple, critical applications throughout the hospital.

As hospitals move toward networks that share resources between information technology (IT) backbones and medical device-based networks to save costs, a there must be a way to ensure that life critical data reach the intended destination with acceptable latency. There are some proprietary solutions that exist, but these unfortunately represent a short term solution as the telecommunication industry continues to follow a strong trend to alight with standards-based solutions, e.g., 802.11e for Quality of Service. While many wireless VoIP manufacturers have been using proprietary Quality of Service, schemes such as always setting the backoff interval to zero, these solutions do not coexist well with non-VoIP data. Similarly, some packet prioritization solutions, such as that offered by Packeteer, provide "traffic shaping", but these proprietary solutions to optimize WLAN bandwidth have been made obsolete with 802.11e.

Further, as hospitals add additional shared applications on the infrastructure, there is no automatic method for IT managers to determine that the Quality of Service level is sufficient for a given application, That is, they can see that the latency on a given node is a certain value, but must manually determine if the applications running on that node support operation with that latency value. As the IEEE 11073 guidance document for medical transport indicates, it is ultimately the end user's responsibility to ensure that the network meets the timing specifications for all the devices on the network.

Historically, biomedical networks and information technology backbone have run separately with the proprietary biomedical networks managed by the biomedical engineer in close cooperation with the medical device manufacturer. As these networks were not connected to the hospital's IT backbone the medical device manufacturer could configure the network in any manner and typically had access to the network to monitor and/or trouble shoot. With shared 802.11 networks that support the enterprise, these solutions are no longer viable as the hospital information technology departments understandably want to control their own network and are not disposed to giving outside access to these networks. Both network security and Health Insurance Portability and Accountability Act (HIPAA) compliance are issues.

There exist many network tools such as HP Open View, Aruba MMS, CiscoWorks LAN Management Solution for analyzing and diagnosing issues with the IT backbone; however, these are typically not available to the medical device manufacturer nor the clinicians whose patients' safety is at risk. Also, for smaller hospitals, these solutions are cost prohibitive.

What is needed is an economical, standards-based solution that allows medical device companies and/or hospital personnel to diagnose issues that occur on systems that use 802.11 and 802.3 networks while maintaining security and privacy of the network. What is further needed is a method to proactively detect problems and alert clinicians and or information technology personnel on a per-application basis of the issue. The clinician alert must be presented in a way that integrates with the clinician's workflow and preferably presented on a device the clinician uses consistently throughout the day.

SUMMARY OF THE INVENTION

The invention comprises, in one form thereof a Simple Network Management Protocol (SNMP)-based data collection and analysis tool that receives performance data from a network component and compares that data to application-specific criteria to determine if the performance is suitable. Alerts may be generated based on the comparison.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION OF A PREFERRED EMBODIMENT

Figure 1:
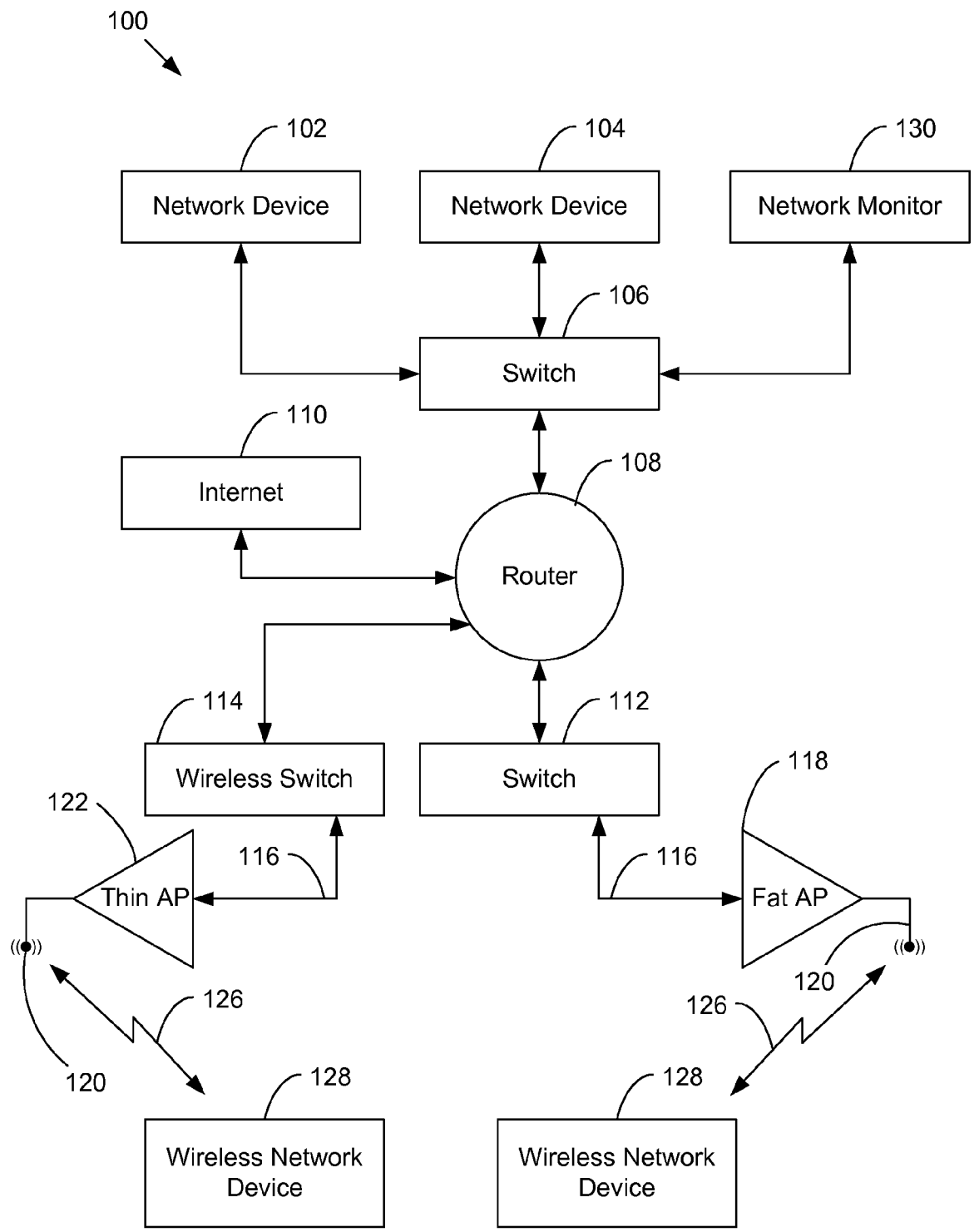
FIG. 1 is a schematic diagram of one network for use with the instant invention.

FIG. 1 shows a sample 802.3 and 802.11 network 100 wherein both a thin Access Point architecture and a Fat Access Point architecture are used. Network 100 includes a first network device 102, a second network device 104, and network monitor 130, which are each connected to one another by switch 106. Network monitor 130 may, for example, be installed on a server. Switch 106 is connected to router 108 which is connected to internet 110. Second switch 112 provides a 802.3 network connection 116 for one or more Fat Access Points 118, each with at least one antenna 120. The wireless switch 114 controls one or more Thin Access Points 122 over a network connection 116, each such Access Point having at least one antenna 120. Both Fat Access Points 118 and thin Access Point 122 can make a wireless network connection 126 to wireless network device 128. With a Fat Access Point architecture, (such as a Cisco AP 1240), all the intelligence for 802.11 communication including encryption, authentication, power management, radio frequency channel selection, and management of wireless network devices 128 is handled in the Access Point. In one embodiment, Access Points function as bridges that convert from 802.11 to an 802.3 network. From the 802.11 side of the bridge, they appear as a layer 2 switch or a hub to the wireless network devices associated with the Access Point. In thin Access Point systems, such as an Aruba AP70 operating with an Aruba 2400 Access Point controller, the Access Point is essentially a radio that transceives 802.11 and converts to 802.3 protocol. All other work is done by a wireless switch 114, alternately called a wireless appliance, and a central Access Point controller.

Generally, network 100 is the collection of network components, such as network devices, network applications, and/or network appliances, that communicate with each other. There may be bridging from one protocol to another, as in 802.11 to/from 802.3, 802.3 to/from PBX (Private Branch eXchange), Wireless Medical Telemetry Service to 802.3, etc. Network components include network devices, network appliances, and network capable applications.

Network devices include personal computers (PCs), personal digital assistants (PDAs), telephones, servers, laptops, patient monitors, wireless Infusion pumps, bridges and the like. These devices are all generally endpoints in a network, but occasionally have multiple network connections, allowing them to function as both network devices and network appliances.

Network appliances, such as 802.11 network appliances, include routers, switches and hubs. Other networks, such as Cellular, Bluetooth, WiMax, Ultrawideband, Wide Area Networks, and other technologies all provide the same net effect: data is transferred from/to a first network device to/from a second network device.

Network applications include software running on a network device or appliance that requires a network connection to operate. Examples include streaming audio such as internet radio, wireless VoIP telephones, web browsers and patient monitoring when the monitor connects to a network device such as another monitor or a central station.

Figure 2:
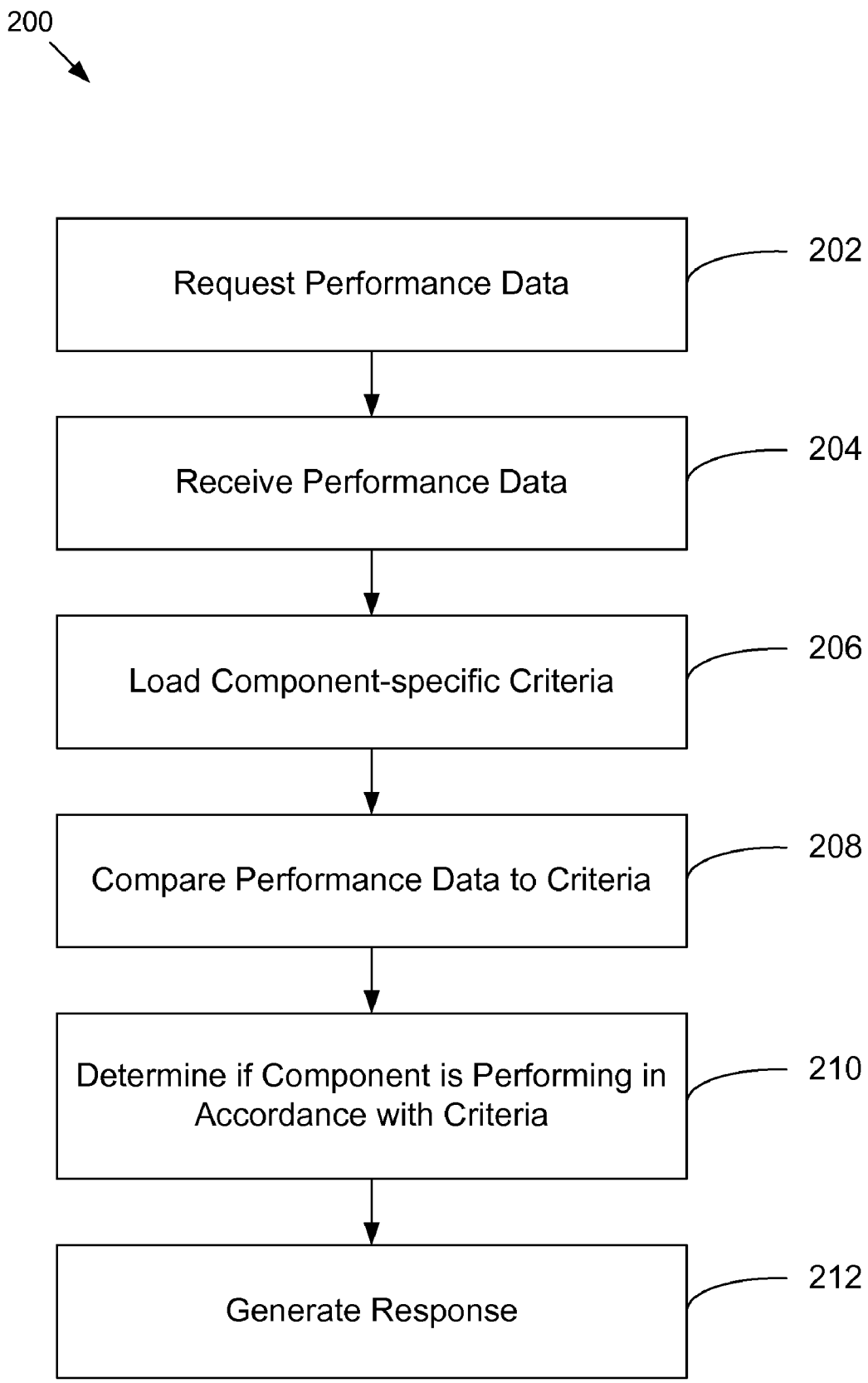
FIG. 2 is a flow diagram of one process of the invention.

Referring again to FIG. 1, network monitor 130 receives performance data from applications (such as software programs) running on certain network components (such as network devices 102 and/or 104 or network appliances) and uses this data to determine if the applications are performing in accordance with expectations. Process 200, depicted in FIG. 2, illustrates one method of performing such monitoring. We note that either the physical network component or the software running on the network component may dictate the performance levels required. For example, a radio may have a receiver sensitivity of −90 dBm, so the signal must be strong compared to −90 dBm. The software using that network component may be tolerant of 3-seconds of dropped data, but not more. In this case, both −90 dBm and 3-seconds on dropped data are criteria by which to judge the suitability of the network to support this network application. As such, descriptions herein may refer to device, appliance, or application criteria.

FIG. 2 is a depiction of process 200 for monitoring applications on a network. In one embodiment, process 200 is initiated by performing step 202, wherein the network monitor requests performance data from a network component. For example, the performance data so requested may include: up time, network identifiers such as BSSID, IP address and Location Code, connection duration, authentication state, authentication method, number of packets received, number of packets received with errors, number of successfully transmitted packets, number of failed ACKs on transmitted packets, peak and average transmit and receive throughput on the radio, number of retransmissions, number of fragmented packets, RSSI, number of devices on the AP, ESSID, and packet fragmentation threshold.

Referring again to FIG. 2, process 200 includes step 204 wherein the network monitor receives performance data. In one embodiment, the performance data was transmitted in response to a request (step 202). In another embodiment, no request was made by the network component (i.e., step 202 is optional), but the network component automatically transmitted the performance data.

In step 206 of process 200, once communication with the network component has been properly established, then component-specific criteria is loaded into the memory of the network monitor. The network monitor includes a plurality of component-specific criteria—one such criteria for each unique network component to be monitored. Each component-specific criteria is comprised of one or more elements against which a piece of performance data may be compared. The network monitor selects the current criteria based upon the identity of the network component currently under examination.

Figure 3:
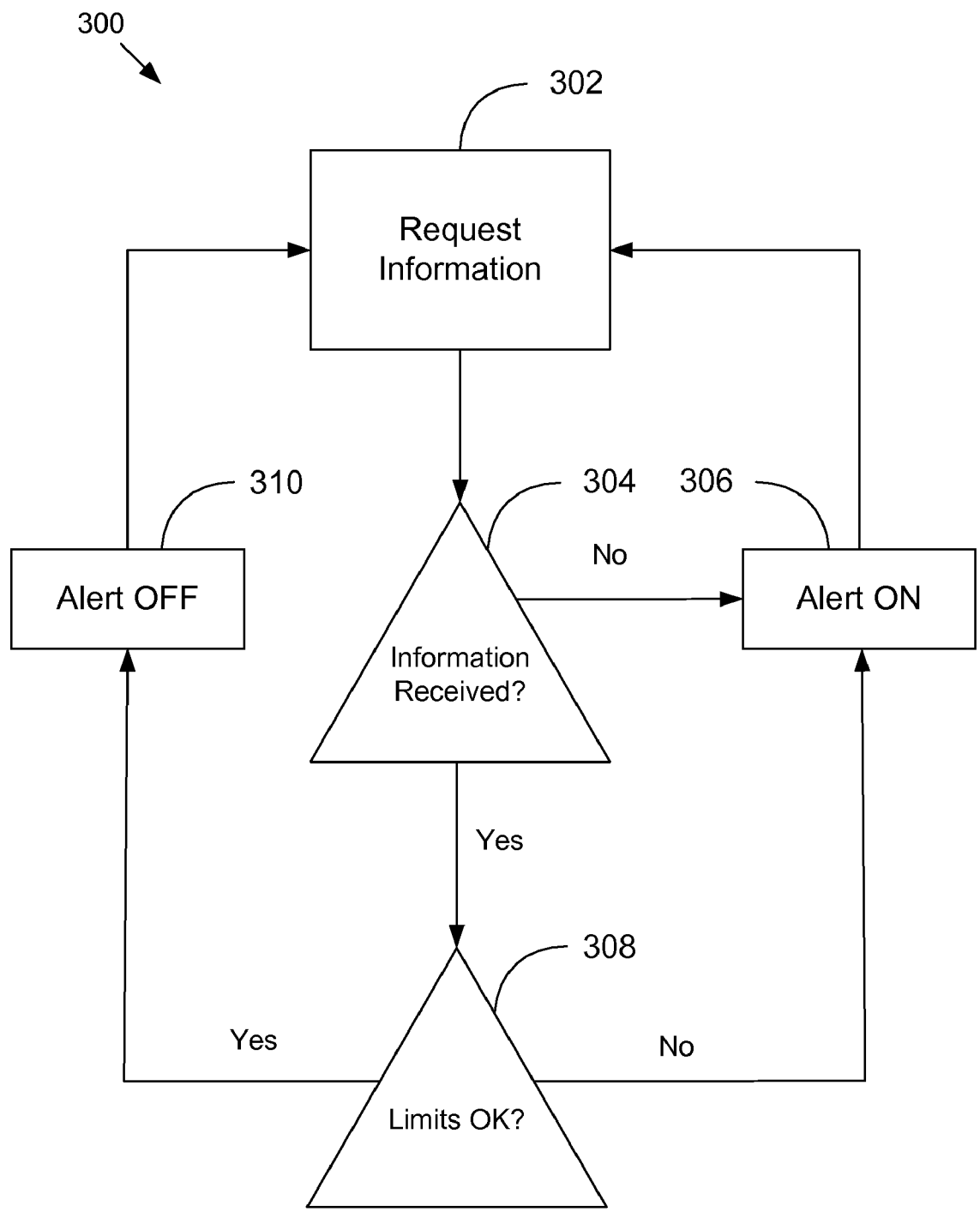
FIG. 3 is another flow diagram of another process of the invention.

In step 208, once the component-specific criteria has been loaded, the received performance data is compared to the current criteria. In step 210, a determination is made as to whether the performance data meets the current criteria. Depending on the outcome of this determination, a response is generated in step 212. If the criteria are met, then a first response is generated. If the criteria are not met, then a second response is generated. For example, the first response may be the triggering of an alarm and the second response is an "All OK" signal. In another embodiment, the first response is an "All OK" signal and the second response is the generation of an alarm. In certain embodiments, an operational alert process is performed after the execution of step 202, but prior to the execution of step 204. Such an operational alert process is depicted in FIG. 3. These component-level performance alerts may be delivered to both a central location (e.g., a system log (syslog) server) and also to the impacted component. For example, if patient waveform data are adversely affected, then the associated patient monitor and its waveform display on a server annunciate an alert, while other monitors and server displays are not affected. The terms "alarm" or "alert" refer to any detectable condition that indicates the existence of a specified occurrence. The alarms include equipment-based alerts that indicate a potential issue with a piece of equipment or patient based alarms that indicate a potential issue with a particular patient. Such alarms include visual signals (text appearing on a screen, color changes, flashing indictors, and the like), electronic messages (e-mails, pages, and the like), buzzers, and other suitable stimuli.

The network performance analysis process could be implemented in a single software module, or distributed across multiple modules. In one embodiment, the data and data analysis as a function of application is performed separately from the application. In another embodiment, the application for which timing is critical could receive the timing data, via an API or by reading the log files or other method known to those skilled in the art, and the application runs the filter that causes the alerts to occur. This application can run on one or more servers with one or more applications on each server. An example is a patient monitoring system where the application is the server-side patient waveform display. Perhaps sixty of these applications run on a single server, each connected to a patient monitor. The network monitor can also run on this server and monitor the activity for all sixty patient monitoring links. As described previously, the alerts can be applied to just the patient waveform windows and patient monitors that experience network issues, as might occur when a single access point is blocked by a metal food cart.

FIG. 3 shows a flow diagram of process 300 for the network monitor to ensure that the network component is operational, and issuing an alert if it is not. In the embodiment depicted in FIG. 3, information is requested in step 302. Such information may be the performance data of step 202. Alternatively, such information may be non-performance data, such as a simple "ping" signal. In step 304 a determination is made as to whether the network component is responsive. If not, then an alert is issued in step 306. If data is received, then the network monitor then evaluates the returned item against some criteria in step 308, e.g., CPU load within limits. If the signal from the network appliance is not within limits, an alert is issued. If the signal is within limits (step 306), then no alert is issued and/or existing alerts are turned off (step 310). The network monitor runs in a continuous loop and requests information again (step 302 is repeated). In the embodiment depicted in FIG. 3, a dropped packet could cause an alert even if the network component is functioning properly and the information is requested at a very high sampling rate, which could adversely impact the performance of the network monitor, intermediate network appliances, and the monitored network component. In another embodiment, steps 302 and 304 are repeated multiple times before an alert is generated (step 306). The information requested can of course be more extensive than a simple operational check and may include port status, CPU (Central Processing Unit) load levels, FW version, DHCP (Dynamic Host Configuration Protocol) configuration, network statistics including packet rates, size, packet error rates, and other parameters for network appliances and network devices known to those skilled in the art.

Figure 4:
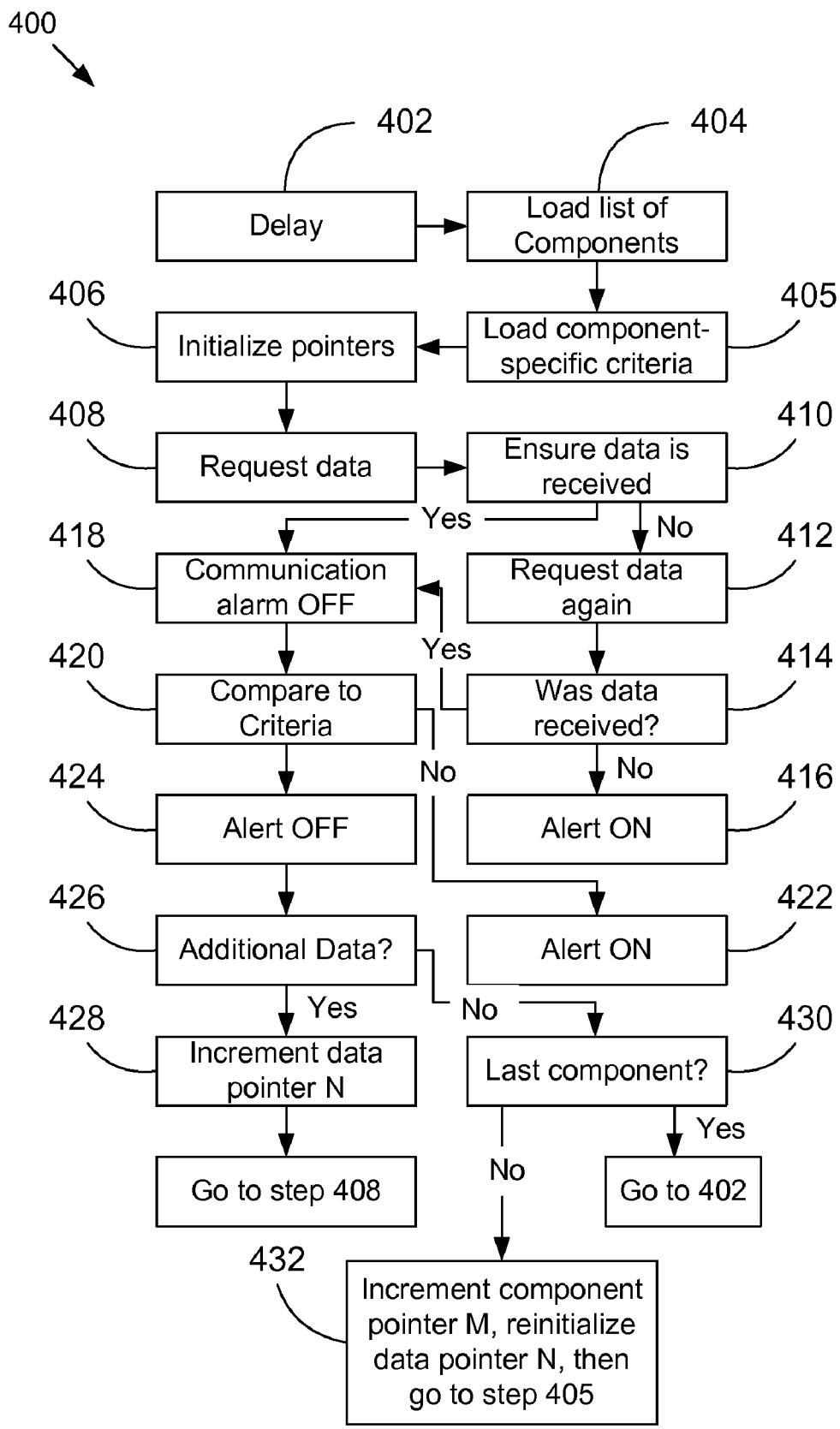
FIG. 4 is yet another flow diagram of another process of the invention.

FIG. 4 shows a flow diagram of process 400 for a network monitor to ensure network components are performing within tolerance. The network monitor has access to a list of the network components of interest and runs through the entire list, requesting the appropriate information for each network component in turn before progressing to the next component. In the embodiment depicted in FIG. 4, the network monitor progresses through such list by incrementing the pointer M (which corresponds to a specific network component) and by incrementing the pointer N (which corresponds to a particular piece of performance data of interest). Alternately, it could request some performance data, e.g. priority data, from each network component and then later or at a different interval request other performance data from each network component.

Referring again to FIG. 4, a delay is introduced in step 402 which allows queries to occur periodically. Delays could be implemented at other areas, such as between each data request, between changing from a network appliance, between each network appliance, etc. Any suitable delay may be used. One should select a delay that is short enough to permit sufficiently frequent checks of the network components, while not selecting a delay that is so short as to consume the bandwidth of the network, and thus impact network performance.

In step 404, the network monitor loads from memory or otherwise acquires the list of components to monitor. In one embodiment, such a list of components is loaded from a configuration file. Advantageously, such a list can be constructed so as to monitor only those components of interest, while ignoring those components which are not of interest. Therefore, while some network components, such as certain switches may not be monitored, they could be. Further, monitoring of a down-stream network component can occur through multiple monitored and/or unmonitored network components. Assuming wireless device performance is what is to be monitored in a thin AP architecture, from the list of monitored network device, the network monitor extracts the name(s) or address(es) of the AP controllers. This may be done for example by identifying the MAC addresses, or by having field in the list of monitored network components include the network component type, (e.g., wireless controller, Fat Access Point, Switch, Router). From the controller(s) list, the network monitor extracts a list of all Access Points that report to the controller(s). If there is a master controller with a hierarchical system of controllers under it, then the network monitor need only be concerned with the name or address of the master controller—slave controllers and their thin Access Points need not be in the list of monitored components as many master controllers aggregate all their data, including failed communication conditions. If we consider Fat Access Points 208 as controllers with a single Access Point, then this discussion may he applied to a Fat Access Point architecture as well.

Once the network monitor has a list of controllers, for example from reading a configuration file, then it extracts from them a list of Access Points. For Fat Access Points, the controller list is the Access Point list. With this list of Access Points, the components associated with each Access Point may be combined to form a definition table, typically from a table provided by controller. With a definition table of components to be monitored, the component list may be filtered so that only selected components are monitored. For example, one's installation may use Symbol VoIP telephones and this VoIP application is the only one in which time-critical data exists. Filtering for a MAC prefix of 00:A0:F8 (the prefix assigned to Symbol) reduces the list of all components to just the VoIP telephones which are the selected components. If a real-time list of the network components that are in communication with the application is available, then the definition table of selected devices to be monitored may be augmented by adding to it this real-time list.

The network monitor loads the criteria which corresponds to the currently selected component in step 405. Such criteria will be applied in step 420. Advantageously, the network monitor can select only certain performance data for analysis. Alternately, all data for all network components for all Access Points may be downloaded, but this is not a preferred solution. A large number of network components may exist and downloading the full data complement for only the components of import speeds response of the network monitor, decreases the load on the network, and decreases the load on the network component itself.

Once the current component and the current piece of performance data are selected, the network monitor sets a component pointer (M) and a performance data pointer (N) to initial values in step 406. For example, on the first iteration of the loop, M=1 and N=1. After these parameters have been initialized, the network monitor requests the performance data for the current (M,N) in step 408.

In step 410, a check is made to ensure the performance data was received. If the data is not received, then one additional attempt is made to acquire the data (step 412). The results of the second attempt is queried in step 414. If this second attempt also fails, then an alert tied to that component and that data, denoted (M,N) is turned on (step 416). Note that this step could allow for multiple additional attempts and/or to delay for a certain period of time before reporting the alert and/or a delay between each of the multiple additional attempts. After the alarm is executed in step 416, an appropriate continuation step may be executed, such as step 426, which continues the monitoring process 400.

If the requested data is received within the allowed time and/or number of attempts, then any associated alert from a prior failed communication result is turned off (step 418). If no alarm was active, then an "off" signal may be optionally transmitted, as such a signal is non-productive. Once the network monitor has received the performance data, the data are compared against the current component-specific criteria in step 420. If the data fails to meet the criteria, alert (M,N) is turned on (step 422). This alert is specific to component M and data N. If the data meets the criteria, then alert (M,N) is turned off (step 424). If no alarm was active, then an "off" signal may be optionally transmitted, as such a signal is non-productive. In other embodiments, the reverse operation is executed. For example, the alert is activated if the data meets the criteria.

In step 426 a determination is made as to whether additional data are desired for the current network component. If additional performance data is desired, then the performance data pointer, N, is incremented (step 428) while the value of M is maintained and the corresponding data is requested (step 408 is repeated). If all information for this component has been requested and this is not the last component on the list (checked in step 430), then we move to the next component by incrementing the component pointer, M and resetting the performance data counter (step 432) and thereafter repeating step 408. Otherwise, if the current component is the last component on the list, step 402 is executed and the entire process begins again. The values of M and N will be reinitialized in step 406. Readers should appreciate that this flow is one embodiment of many acceptable embodiments in that the order of requesting data can be changed, alerts could be enabled/disabled for all devices en masse just before re-starting the entire process, etc, while preserving the same operation of the invention.

Figure 5:
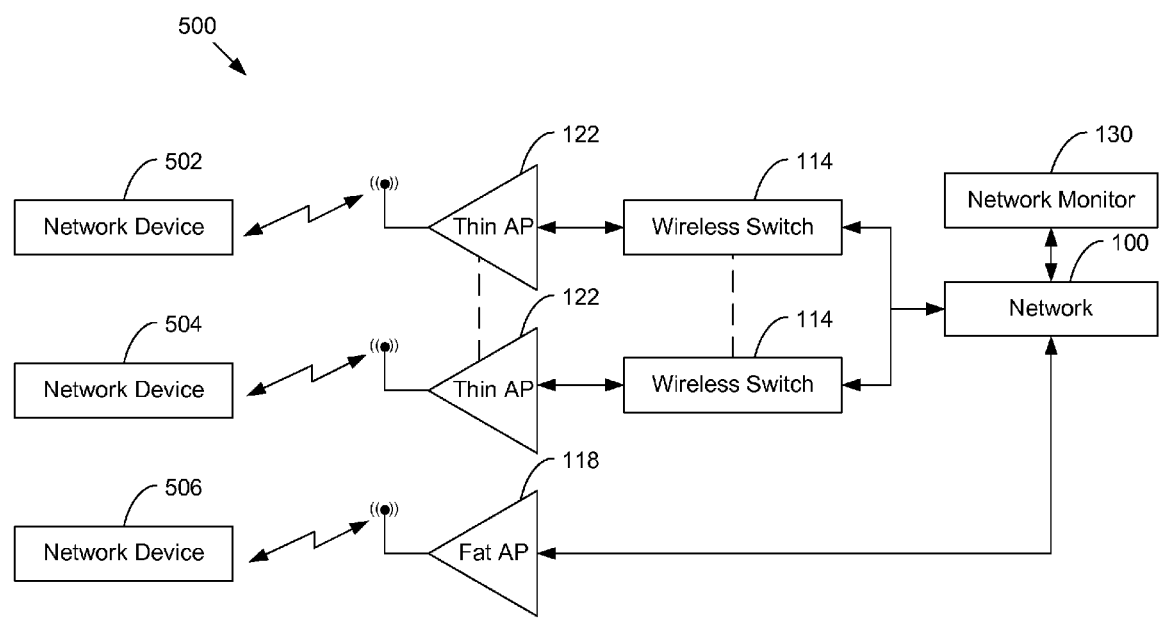
FIG. 5 is a depiction of another network for use with the instant invention.

Performance data are available for both network devices and network appliances. FIG. 5 shows a mixed 802.11 and 802.3 network 500 with a network monitor that includes network devices 502, 504, and 506 as well as network appliances instantiated in the wireless switches 114, the thin Access Points 122, and the Fat Access Point 118. Note that network monitor 130 can work across other types of bridged networks, such as a Wide Area Network, GSM (Global System for Mobile Communications) network, or Wireless Medical Telemetry Service (WMTS) network. Similarly, the larger networks than that shown in FIG. 5 could be used in conjunction with the instant invention. However, to avoid undue complication, FIG. 5 focuses on obtaining component-specific performance data for the wireless devices 502, 504, and 506 and those applications that are running time sensitive processes. While knowing a network device has stopped operation is important for maintaining the network, if an application is not affected by that device failure, it may not be critical in this example. For example, when radio frequency coverage is provided by multiple Access Points and one fails, as long as there is another to provide the necessary radio frequency coverage and bandwidth, there is no reason to raise a component-specific equipment alert. In FIG. 5, the network devices 502, 504, and 506 are wireless and provide network information through various network appliances, namely the Access Point 122, wireless switch 114 (for the thin Access Points), and through the Fat Access Point 118, to the network 100. We also note that a thin Access Point architecture controller may actually include a group of controllers and further, that this group of controllers may have a hierarchical structure where a master wireless switch aggregates all data for all slave controllers and their connected Access Points so that the entire thin Access Point portion of the network may be logically considered to run from the single master. For example a master controller with multiple slave controllers allows one to interrogate just the master controller to request all data for all slave controllers, their respective Access Points and also the network devices wirelessly attached to each Access Point. In a Fat Access Point architecture, each Access Point may be considered a single controller that controls a single Access Point, namely itself.

Figure 6:
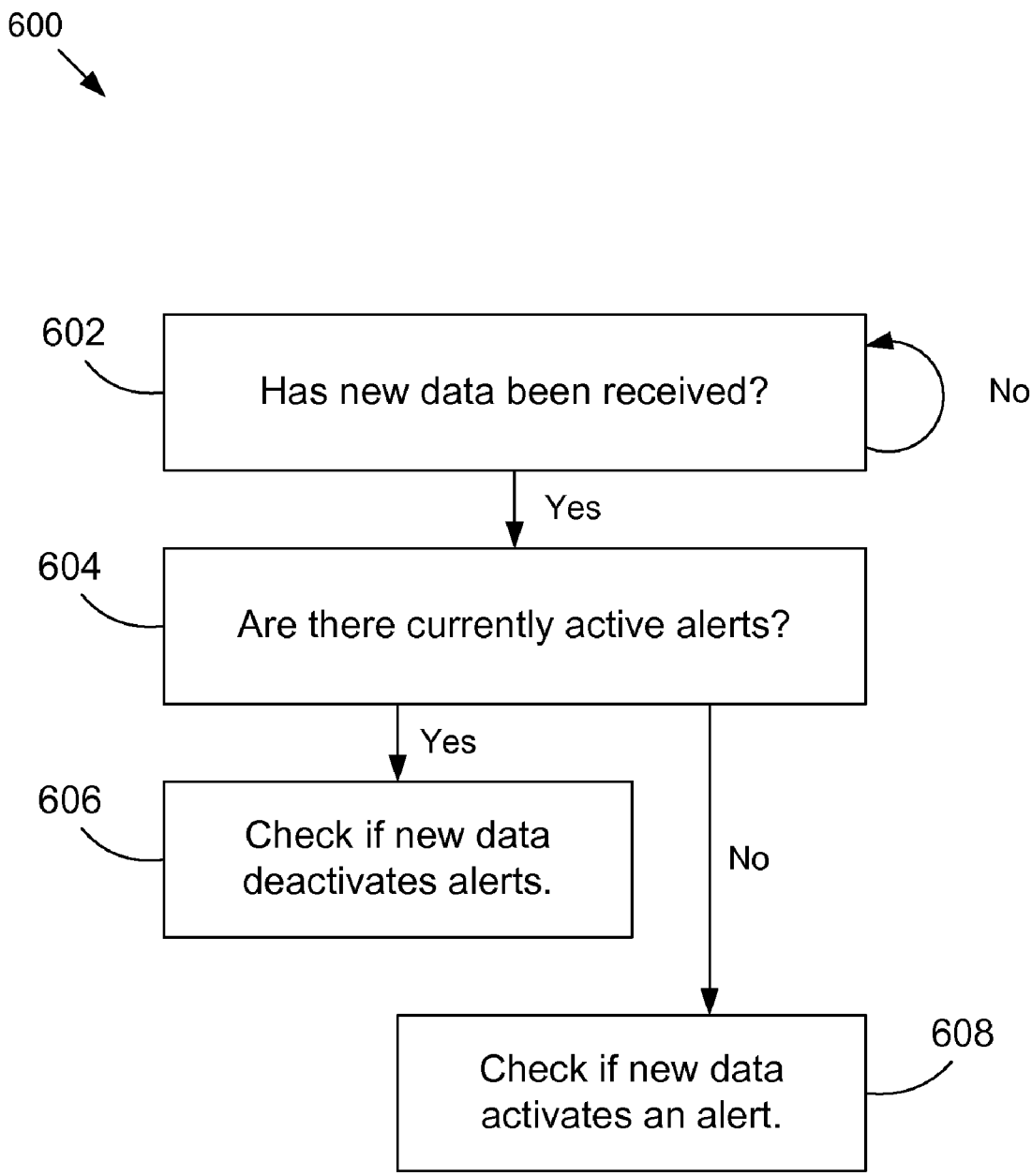
FIG. 6, FIG. 6A, and FIG. 6B are flow diagrams of various alarm management processes.

The flow diagram in FIG. 6 illustrates how alert states may be evaluated and turned on/off as a function of performance data acquired by another process, for example that illustrated in FIG. 4 or FIG. 5. In the example process illustrated in FIG. 6, a single application is running on one Monitored Wireless Network Device. The process 600 is repeated for each component running an application that has timing critical performance requirements.

As shown in FIG. 6, the network monitor is watching for new data to be received in step 602. When such data are received, the monitor checks to see if any existing alerts are currently being displayed. Such a check for alerts occurs in step 604. If an alert is currently active, then sub-process 606 is executed, wherein the specific type of alert is determined and appropriate action is taken. Sub-process 606 will be discussed in additional detail elsewhere in this specification. If no such alert is currently active, then sub-process 608 is executed, wherein the network monitor watches for data reliability and timing specifications between wireless network devices and an application server. Sub-process 608 will be discussed in additional detail elsewhere in this specification.

Figure 6A:
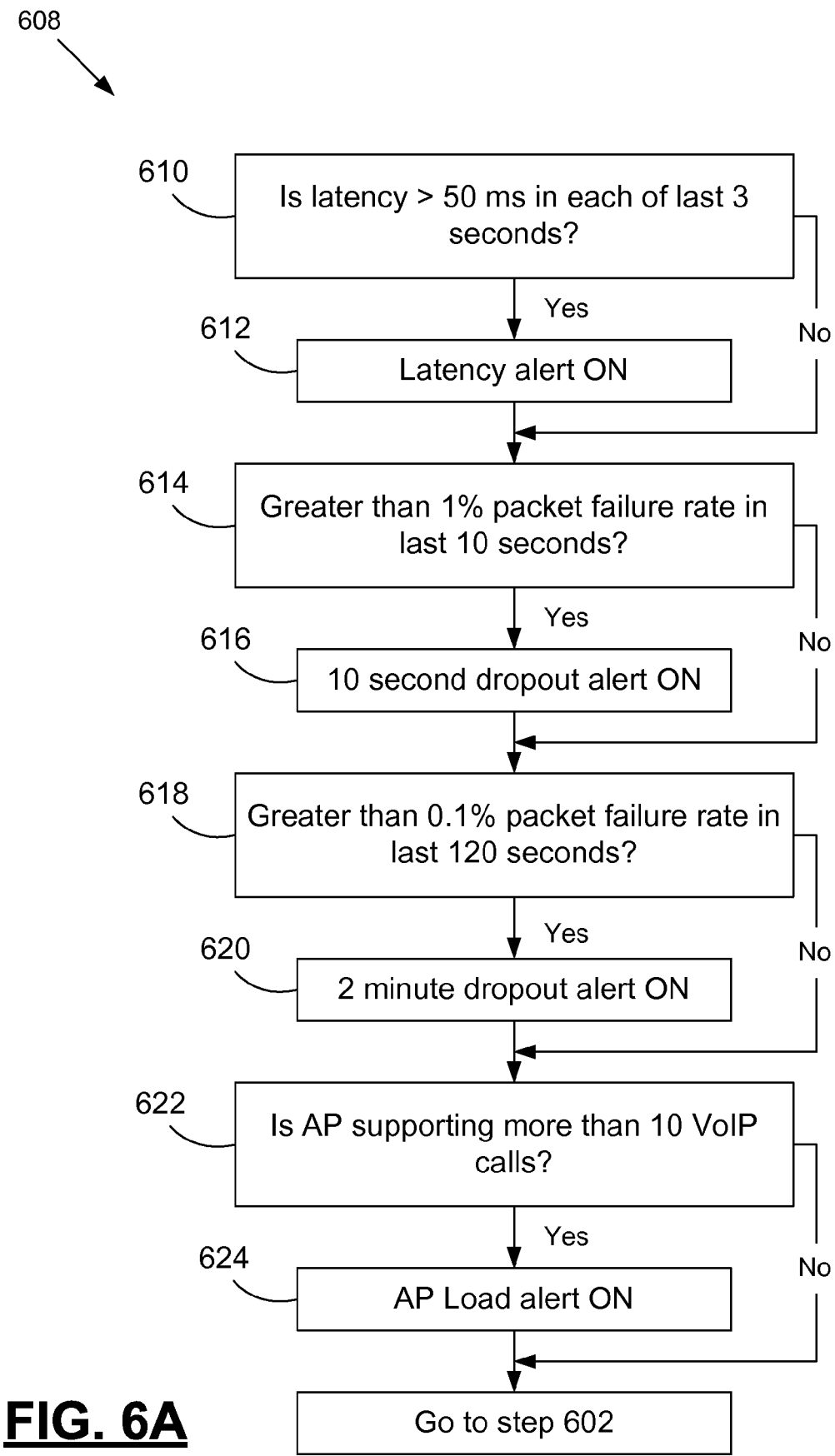

In step 610 of sub-process 608 (see FIG. 6A), the latency of the performance data is checked against an acceptable latency limit, which is specified in the component-specific criteria discussed elsewhere in this specification. In the example depicted in FIG. 6A, the latency limit is specified to be less than 50 ms in each of the last three seconds. At least one instance of excessive latency occurs in each of 3 seconds in a row, is considered reportable. If the latency is not acceptable, then a latency alert is activated in step 612. If the latency is within tolerance, then step 614 is executed, wherein the next piece of performance data is checked against the criteria. In this manner, multiple steps may be executed to perform multiple comparisons of the performance data to the component-specific criteria.

In steps 614 and 618 of sub-process 608, the packet failure rate is compared to several component specific criterion. These criteria identify an acceptable packet failure rate not to exceed 0.1% over any 2-minute period (step 618, generating an alert in step 620) or over 1% over any 10-second period (step 614, generating an alert in step 616). Note that packet failures at the MAC level result in retries so that a 1% packet failure rate at the MAC level may result in a much lower packet failure rate, perhaps, 0.1%, at the application level. This two-tiered packet error rate or other similar method provides for fast response to a network issue, such as a brown-out with a relatively high threshold so that noise spikes are not a factor, while still enforcing a more stringent, long-term requirement.

In step 622, a check is made for an excess number of high-demand components, such as VoIP components on a single Access Point. In the example depicted in FIG. 6A, if more than ten VoIPs are running on a single access point, then an alert is generated in step 624.

Figure 6B:
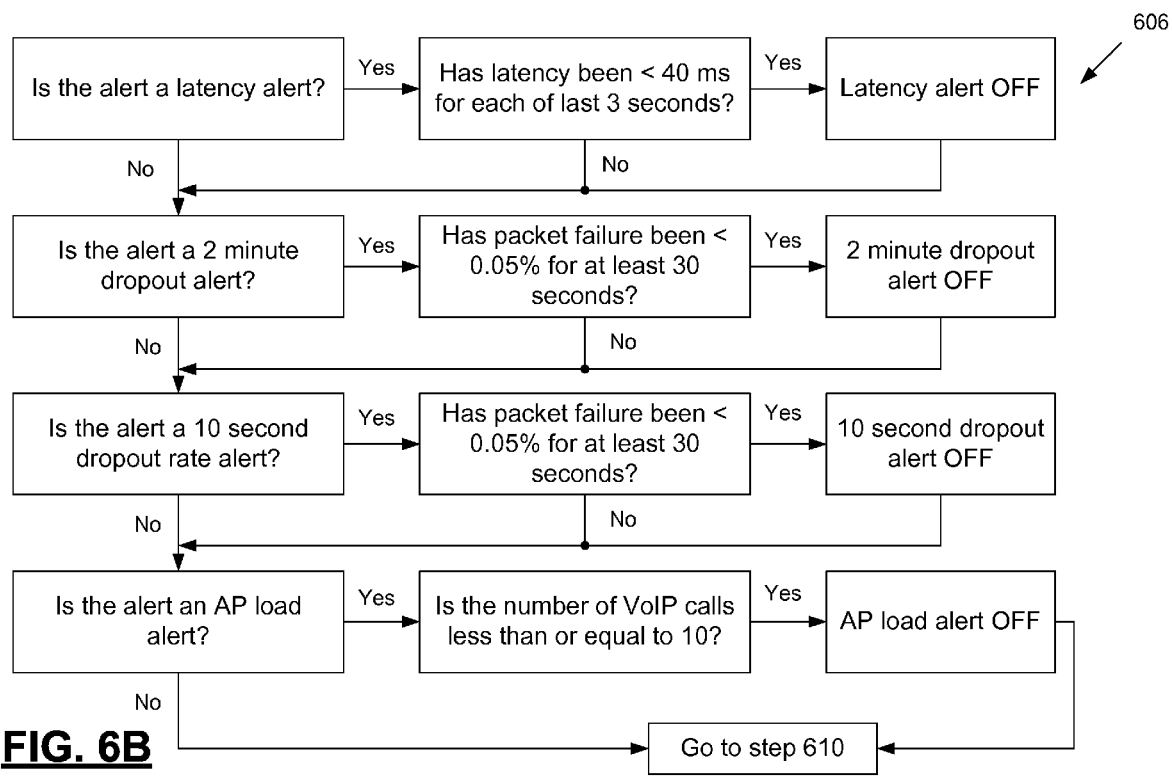

Referring now to FIG. 6B, and to the sub-process 606 depicted therein, existing alerts are processed. To ensure the condition that caused the alert is truly resolved, once reported, the condition must be resolved such that it satisfies a certain criteria. The criteria for turning off the alert may be different than the criteria that generated the alert. For example, for the latency alert generated in step 612, the latency must remain below 40 ms for 3 seconds for the alert to be deactivated. With respect to the drop-out alert generated in step 616, dropout rates must remain below 0.05% for 30 seconds to remove such a dropout alert. Other criteria for deactivating the alerts are illustrated in FIG. 6B. Requiring a threshold to be met for a certain amount of time is a "hold-off" delay period.

In certain embodiments, it is advantageous to use a "hold-off" delay to prevent a certain alert from being inappropriately triggered. For example, the invention described here could run on devices such as HP OpenView, which allows this network monitoring tool to turn the green, "all OK" indicator off for a specific access point if VoIP applications are experiencing more than a 50 ms delay. However, it would be undesirable to disable the "all OK" indicator if only a single packet experiences a 51 ms delay. On the other hand, if many packets in a row are above 50 ms (resulting in the "all OK" indicator being in the off state), and then a single packet transmission has 49 ms delay, the "all OK" indicator should remain off. This is accomplished by including a hold-off delay to turn the "all OK" indicator on and off. For example, only after 500 ms of having at least one packet experience latency >50 ms does the "all OK" indicator turn off. Only after 1000 ms of having no more than 1 packet experience a latency of >50 ms does the "all OK" indicator turn back on. The values for the on and off hold-offs can be different and tuned for the specific application and network. In addition to hold-off delays, the hysteresis in the trip levels may also be used to control nuisance alarms.

The term "hysteresis" refers to a non-time based condition wherein the state of the displayed or examined value is a function of the recent history. For example, a Schmitt trigger is a comparator circuit that incorporates hysteresis. When the input is higher than a certain threshold, the output is high. When the input is below another (lower) threshold, the input is low. When the input is between the two levels, the output does not change. This is useful in logic circuits where there is noise on the lines so that the logic output does not change simply because of noise. In contrast, a hold-off requires that the change threshold is met for a period of time before the output changes states. Since these are application-specific performance decisions, the application-performance monitor is configurable to accept different parameters for different applications. These parameters may be supplied through a configuration file, API, or other method known to those skilled in the art.

Hold-offs and hysteresis can be used to address systemic packet loss. Systemic packet loss may occur in a block, or perhaps once every 100 ms. How many times can a packet loss occur and in what duration? That is, losing ten packets in a one-hour conversation is likely acceptable, but losing ten packets per 5 seconds is not. In such an example, a threshold criteria may be ten occurrences with a hold-off of 5 seconds. For example, the packet loss may drop to an acceptable level such that the "all OK" indicator is turned off (or an alert being annunciated, which we will consider as the same). One must determine how long the "all OK" indicator should remain off, should it turn back on quickly or not, and what is the definition of "all OK"? This is an application-specific decision, but obviously it should not stay off forever and should remain on long enough that the same alarm doesn't occur a few seconds later. Imagine the information technology worker who receives hundreds of e-mailed alert messages indicating that the network is failing because one VoIP phone for a few minutes was in an area of poor radio frequency coverage. This should preferably create a single alarm (such as an e-mail), and on/off hysteresis, optionally combined with a hold-off, is one solution. The threshold for turning the "all OK" indicator on requires a better network performance level than caused it to turn off. That is, the network must be noticeably improved. By providing hold-off times and hysteresis configuration variables, the application specific network monitor can be tuned to reduce the number of nuisance alarms.

In one embodiment, logs of the performance data are kept. Such logs may be analyzed. Based on this analysis, a list of components of interest may be constructed. Alternatively or additionally, trends in the performance of the network can be determined and potential problems may be proactively identified before they mature into actual issues.

Since the data are logged (or stored in memory), the data can be trended and/or compared against a baseline. This baseline may be, for example, taken at the time of installation validation. This allows the network monitor to trend data, report, and/or alert when the trends become unstable. With the addition of trending functionality to the network monitor, a sudden increase in packet load (even if still within limits) can indicate that network problems will occur soon. More likely, latency and dropped packets increase as new applications are put on a wireless network. Notification of this trend of increasing demand allows IT professionals to respond to upcoming issues rather than react to emergencies. Hold-off delays and hysteresis are again useful to prevent annunciating the same alert many times for the same event. In one embodiment, the radio frequency coverage is baselined along with the timing specifications. The network performance analysis process can then correlate increased noise, decreased signal strength or other radio frequency parameter with dropout as a function of time and location.

In some embodiments, performance data is stored over long periods of time. Trending such long-term data is a useful tool to identify when a system change has disrupted operation. For example, if typical wireless cyclic redundancy code (CRC) check errors are 10 percent and thereafter changes to 20 percent on a particular set of Access Points for a period of a few hours on the same day every week, then the information technologist has a clue to look for a temporal change in the radio frequency environment on that day of the week. Note that the list of wireless network devices communicating with each Access Point may be extracted each time a single Access Point datum is received, or may be batched after all Access Point data is received. Once the data for the monitored wireless network devices and Access Points of import have been acquired, they are compared against the performance specifications for the applications running on those devices as describe elsewhere in this specification. The network component type may be derived, as above, from the manufacturer's MAC address prefix, it may be defined in a configuration file, or it may be derived by inspection of what traffic flows. For example, User Datagram Protocol (UDP) on port 7711 suggests a Welch Allyn Patient Monitoring System. If an HL7 server exists on a certain address, then data to/from this is HL7 data. In this example, a configuration file provides the network performance specifications for each type of device.

Additional data to log and trend may be obtained by resolving the packet transit time from source to destination. Typically, each device can only report on its own delays. However, when network components are chained in series, if one end of the chain pings the other and logs the response time, an indicator of the health of the entire chain is established. This does add network load and so preferentially, existing packet response times are used, rather than requesting new packets. For example in streaming data applications, typically an occasional keep-alive packet is transmitted. The round-trip time is measured, recorded, and provides another input for the network analysis performance process. Here, the timing data transfer is simplified if the network performance analysis is part of the application.

Trending is also useful to determine when an application that uses pattern recognition is experiencing problems, as the patterns are adversely affected by any missing packets which may occur in any system. Once a missing packet event occurs, there is a recovery time as the patterns are re-established, and during this time, a pattern match may be missed. For example, assuming the recovery time for a certain system is 10 seconds, then missing 1 of every 100 of packets results in pattern recognition being compromised 10 percent of the time. This is worse than missing the same percentage of packets grouped as 10 packets in a row out of every thousand packets—as the analysis is unavailable for 2 percent of the time. Similarly, because heart rate determination is an average of the last 10 or so beat-to-beat intervals, a heart rate analysis that loses one QRS wave per minute over a 10-minute interval may be in error by 10 to 20% (depending on heart rate) for 10 seconds each minute. While this may only be a 1% packet loss, the pattern of packet loss is unacceptable. Given the application's limits, the network monitor can analyze recent historical data performance and determine when a dropout pattern adversely impacts an application to unacceptable levels.

Figure 7:
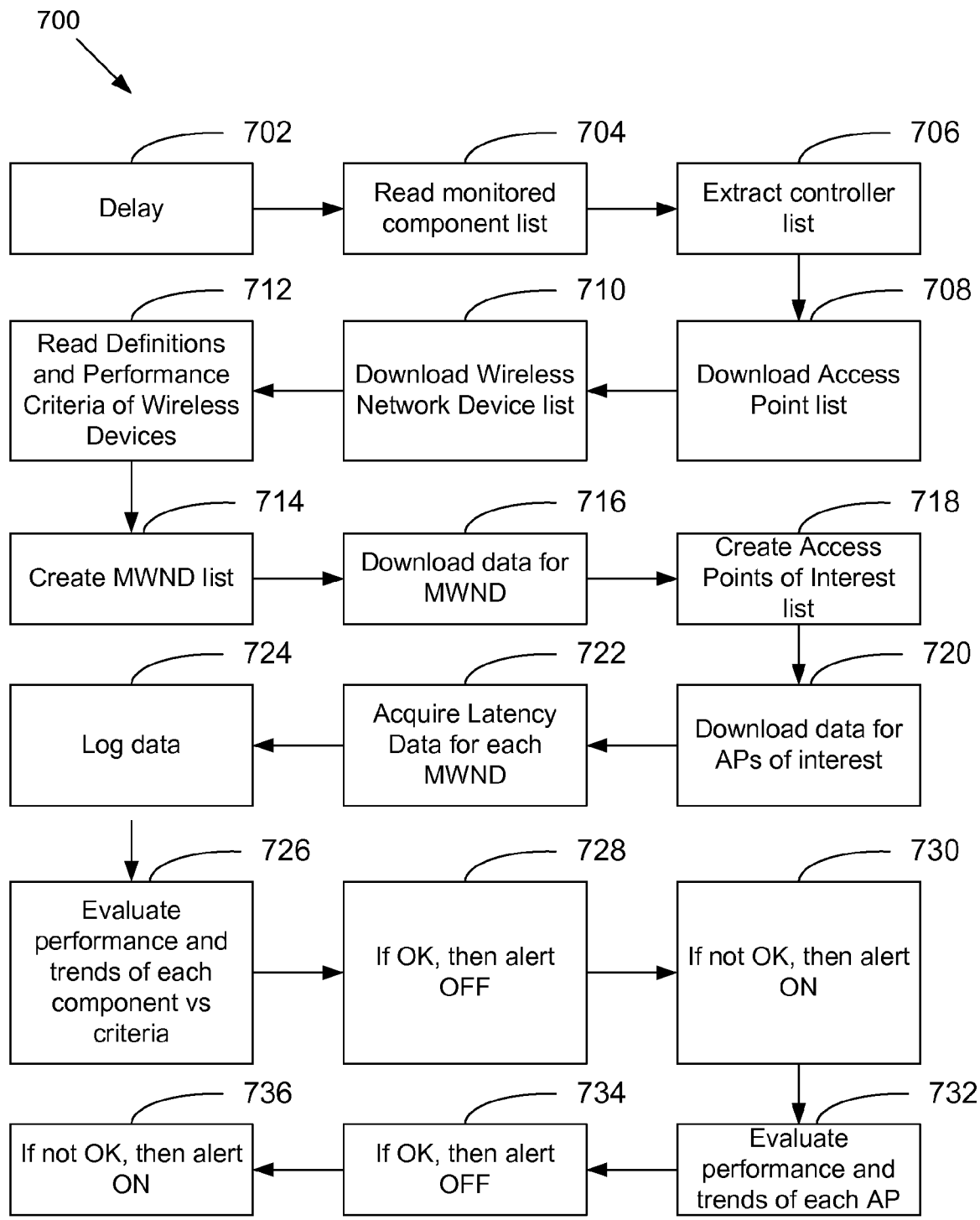
FIG. 7 is another flow diagram of a data management process.

FIG. 7 shows a process 700 whereby a network monitor may monitor the activity of an Access Points and the monitored wireless network components connected to the Access Points. This flow diagram, of course, may be applied to any network that includes Access Points, including those illustrated in the other Figures of this specification. In this flow diagram, the network monitor is provided the list of monitored network devices, e.g., from a configuration file. An alternate solution would be an API to the application the Wireless Networked Devices communicate with. This option provides a real-time list of the Wireless Networked Devices that are to be monitored. In yet another solution, the Network Monitor could be a part of the application that the Wireless Networked Devices communicate with. This has the further advantage that latency can be measured directly.

FIG. 7 shows a flow diagram of process 700 for evaluating the network health for devices on a wireless network. In step 702, a delay is put in place to allow for periodic operation. This delay could be augmented by other delays in the system, or could be instantiated in a different position in the flow. After delay 702, the network monitor reads the monitored component list in step 704 which may include routers, switches, and wireless controllers. In step 706, this list is reduced by extracting just the controllers. For Fat APs, the AP list is the controller list, and step 708 is not required. For thin APs, the controller(s) maintain a list of the APs that are supported by that controller. Alternately, in a hierarchical thin AP architecture, a single master controller maintains a list of all APs supported in that hierarchy and only this single master controller need be queried for its list of Access Points. The AP list is downloaded from the controllers in step 708. Stepping one layer down in the hierarchy, each AP has a table of associated Wireless Networked Devices, and this list is obtained in step 710. Not all wireless networked devices are monitored. While one could download all data for all wireless devices, this consumes bandwidth of both the network and the wireless devices themselves. Preferentially, on performance data for the Monitored Wireless Networked Devices is downloaded and analyzed. The controller determines which wireless networked devices should be monitored and their performance criteria in step 712. As an example, all patient vital signs monitors communicating with a central station may be the set of devices that should be monitored and the IP addresses of these devices are obtained from the central station monitoring application. The Monitored Wireless Networked Device (MWND) list is the set of devices that should be monitored and that are also currently associated with an AP, and the intersection of these two lists is executed in step 714.

Just as some wireless devices need not have their performance monitored, not all data connected to a given wireless device is germane. With the MWND list from step 714 and the list of criteria from step 712, only the performance data that is required for each WMND is downloaded ill step 716. For example, for all patient vital signs monitors, download RSSI and Packet Error rates. Alternatively, all data is downloaded and filtered by the network monitor, but this adds network and computational overhead.

Each MWND is associated with a particular Access Point, and only these APs are of interest, as the performance of APs that are not currently supporting a MWND does not affect the application performance. In step 718, the list of APs which have at least one MWND is created. Based on the criteria from step 712, the appropriate data from each AP of interested is downloaded in step 720.

In step 722, the end-to-end latency is acquired, and this is typically not available from the AP or AP controller. Although latency is critical to many applications, it is not the latency from the Monitored Wireless Network Devices (MWND) to the Network Monitor that matters; rather, it is the latency between two endpoints in the network that is critical. End-to-end latency may be inferred by the network monitor by pinging each endpoint. For patient monitoring applications, the latency is measured between the server at the nurses station that displays all the patients' waveforms to each and every patient monitor. Since the latency is typically dominated by time waiting to access the wireless medium, pinging the MWND by the network monitor may also be sufficient. Preferentially, one endpoint pings the other and reports the round-trip delay to the network monitor, such as via an APT or log file. In the case of the Welch Allyn Acuity Server, command packets are routinely transmitted to the patient devices and the response time to these packets is measured and recorded to provide a latency measure. Alternately, latency may be inferred by measuring the ping response time from a network monitor to the server and also from the network monitor to each MWND. Assuming the primary cause of latency is due to the wireless interface as is often the case, then latency may be inferred simply from the ping response from the network monitor to each MWND.

Now with all the data for this session, it is logged in step 724. Logging the data allows a retrospective analysis and trending of the data. In step 726, historical device data is used to compare trends as well as comparison of current data to the requirements and alerts are turned off and on as appropriate in steps 728 and 730, as was illustrated in FIGS. 2, 3, 4 and 6. Similarly, AP performance data is analyzed and appropriately signaled in steps 732, 734, and 736. Note that the specific order of data retrieval and analysis illustrated in FIG. 7 is merely an example of one process and may be changed while maintaining the current invention.

Figure 8:
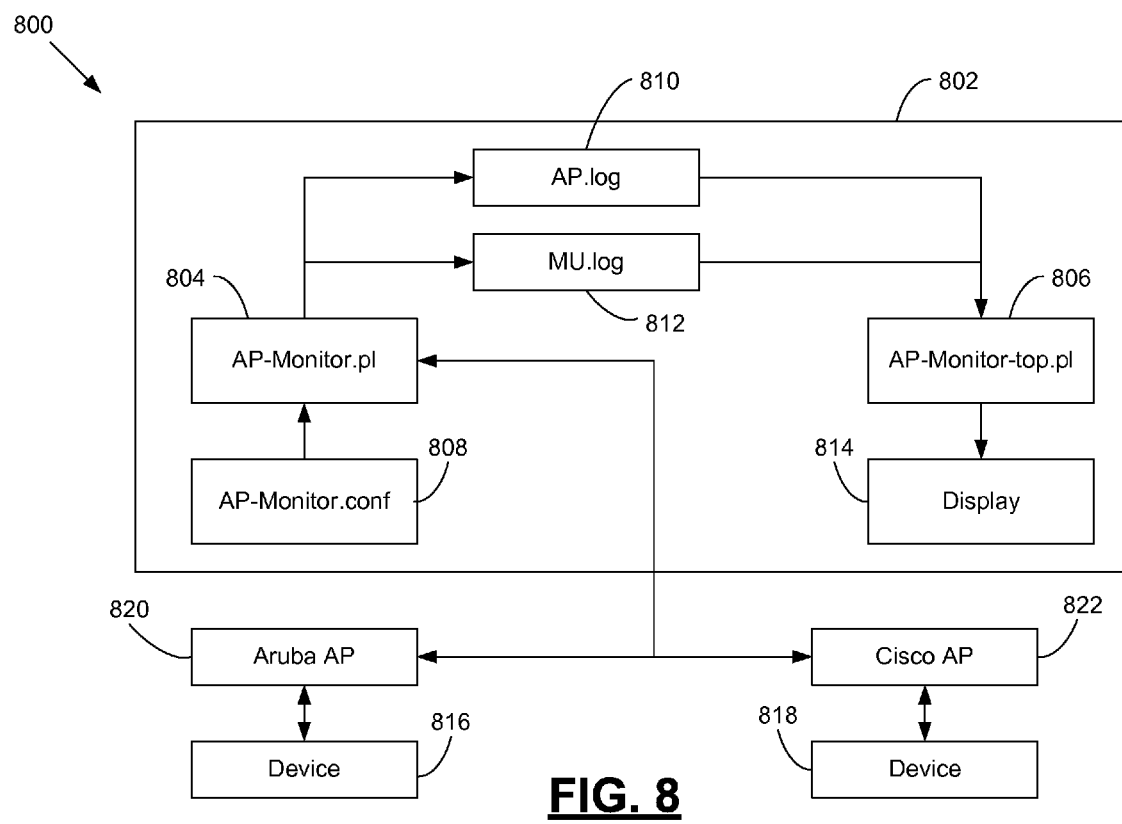
FIG. 8 is a schematic diagram of another network for use with the instant invention.

FIG. 8 shows system 800 which includes performance logging workstation 802 that runs two PERL (Practical Extraction and Report Language) scripts, ap-monitor.pl 804 and ap-monitor-top.pl 806. These PERL scripts use SNMP (Simple Network Management Protocol) toolboxes, and such toolboxes load a Management Information Base (MIBs) (not shown) for each of the components to be queried. The file ap-monitor.conf 808 provides the criteria that specify how to determine if a given application is working properly. The PERL script ap-monitor.pl 806 creates log files, one Access Point-centric (ap.log 810) and one that is Mobile-Unit (MU) centric (mu.log 812). The file ap-monitor.pl 804 obtains performance data concerning devices 816 and 818 through Access Points 820 and 822, as described elsewhere in this specification. Because some vendors use different units of measurement, e.g. packet lost per minute vs packets lost per second, ap-monitor.pl 804 also normalizes the data received from various vendor's MIBs so that AP.log and MU.log contain the same format of data regardless of which vendor's equipment is used.

The Simple Network Management Protocol (SNMP) is a well-established, standards-based solution wherein a Management Information Base (MIB) defines, through a hierarchical addressing structure, the location and data type of all data that the network application exposes. This data can be limited to read-only access of performance data so that no user or application data has its security compromised. An outside device can perform an SNMP read of that address and obtain such data. For example, an Access Point list of the number of mobile units may be at address 1.4.5. However, the Access Point has several mobile units per ESSID, and these may be at 1.4.5.1, 1.4.5.2, 1.4.5.3, etc. Similarly, enterprise-class wireless switches that control many Access Points typically have a hierarchical structure where a master wireless switch can provide, via SNMP, all the data for all the wireless switches and wireless controllers in the enterprise. This is accomplished by interpreting the manufacturer's MIB (Management Information Base). Enterprise class devices from virtually every vendor support SNMP and consequently, SNMP-based management tools provide forward compatibility far above that which proprietary solutions do. While these tools perform admirably, a green light for an Access Point that indicates it is "UP" does not mean it is able to provide message delivery with latency that is acceptable for VoIP, even though file transfer operations work (seemingly) without any issue. The difference is that VoIP is sensitive to cumulative message delays of as little as 50 ms, while file transfer just takes a bit longer to complete.

Ap-monitor-top.pl 806 evaluates the data in ap.log 810 and mu.log 812 to determine what network devices are the extreme (best or worst) performers. In the example illustrated in FIG. 8, the data are parsed by the network parameter in question, such as by most retries, worst Received Signal Strength Indication (RSSI), or lowest signal-to-noise ratio. The output of ap-monitor-top.pl 806 is here shown on an output display 814, but may also be delivered via a log file, data base, or Application Program Interface (API) to another application running on the same workstation or elsewhere in the network. Such other applications may, in turn, evaluate the data against its own performance requirements. Alternately, a second configuration file (not shown) or API provides the application-specific performance specifications to ap-monitor-top.pl 806 and this script also determines if the network performance is adequate for the applications specified. Network performance criteria may include the maximum allowed latency, maximum allowed jitter, minimum bandwidth required, verification of Quality of Service/Terms of Service/Cost of Service or other quality of service tags.

The configuration file, ap-monitor.conf 804 includes specifications for file names, directories to use, Internet Protocol (IP) addresses of the network dapplications to query (such as wireless switches), Polling Time, Polling Limits, and data on which to filter, e.g. Extended Service Set Identification (ESSID), MAC Address Range, Destination address, Source address, etc.

The Log Files ap.log 810 and mu.log 812 contain performance data from the perspective of Access Points and Mobile Units, respectively. File ap.log 810 may contain Date Time, AP MAC Address, AP Basic Service Set Identifier (BSSID), AP IP Address, Extended Service Set Identification (ESSID), Radio type, AP Channel, AP Location, Number of Clients, TxPackets, TxBytes, RxPackets, Bytes, Fragments, Retries, Errors, and other network performance data. File mu.log 812 may contain Date, Time; Client MAC Address, Client BSSID; Mobile Unit (MU) IP Address; ESSID; Radio type; AP Channel; AP Location; Number of Clients; TxPackets; TxBytes; RxPackets; RxBytes; Fragments; Retries; Errors; and the like.

With these examples of what types of information must be considered, we return to the network performance analysis process that defines when network performance is not appropriate. This process gathers information about network performance from network devices such as switches, wireless switches, routers, etc. Using the information in the ap-monitor.conf 808 configuration file, the process parses all the available networks performance information and puts the pertinent information that is requested via the configuration file, e.g. only VoIP calls or only patient waveform data related to a heart monitor, in the log files. We note that this information could be obtained via other methods including hard-coding, via web interface, API, or other methods known to those skilled in the art. A second phase of the process filters the information in the log files against the Timing Specifications defined for each application. These timing specifications and network traffic are typically defined by each device manufacturer and may be stored in ap-monitor.conf 808 or by other means. While the network characteristics for a device/data stream/user are acceptable, no alerts are annunciated. Once the hold off and limit criteria are met, then an alert is annunciated and it stays on until the hold off and off limit criteria are met. As mentioned above, the on-off limit criteria preferably includes hysteresis. We also note that multiple criteria may be required to change alert states.

For each device of import, the actual network performance data are compared to acceptable criteria for the component running on that device, and if the conditions match for applying an alert, then an alert is issued. If an alert has previously been set and conditions match for stopping an alert (e.g., hysteresis, hold off, etc), then, the alert is turned off. Once all data for the network devices are filtered, the Access Point data may be filtered against specifications and alerts annunciated if the specified limits are exceeded. For example, a medical device vendor may have determined that the maximum number of VoIP calls simultaneous with supporting medical monitoring is 5 calls. If an Access Point simultaneously supports more than 5 calls and medical monitoring devices, then an alert would be issued for the medical monitoring devices on that Access Point. Preferably, only data for Access Points supporting a connection to a monitored wireless network device are analyzed as this reduces the processing and network overhead. If an alert has previously been set and conditions match for stopping an alert, then, the alert is turned off. The filtered data are logged and then the sequence re-starts. The Access Point data is downloaded again as an Access Point may have been added since the last check. Also, a wait state may be used so that the network queries do not burden the network. We note that the same results may be accomplished, namely application-specific alerts, with different orders of filtering, logging, and trending data.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A network monitoring system for monitoring a medical network to determine if connected network components are adequately performing without otherwise burdening said network by performing the method comprising the steps of:
   a. connecting said system to said network, said medical network comprising a plurality of connected network components, said network components including network devices comprising patient monitoring devices and at least one of wireless infusion pumps, PCs, telephones, PDAs, monitoring stations and servers for obtaining and transmitting life critical data, including waveform data, on said network, network appliances comprising at least one of routers, switches, and hubs for controlling data flow along said network and network-capable applications comprising software run on said network devices and network appliances on said network, wherein said connecting step includes the step of installing said system on a central monitoring system of a medical facility,
   b. measuring the actual network performance of data typically traversing the network, c. receiving network performance data from applications running on at least one connected network component over said network, said performance data relating solely to said first network component's connectivity with said network, with at least one other connected network component, d. selecting a component-specific criteria, wherein the component-specific criteria is selected from a plurality of component-specific criteria based upon the unique identity of the first network component and relating to operational aspects of said network component on the network, such that the selected component-specific criteria corresponds to the first network component, e. comparing the network performance data from the first network component to the selected component-specific criteria, f. determining if the network performance data from the first network component satisfies the selected component-specific criteria, g. generating a first response if the network performance data satisfies the selected component-specific criteria and generating a second response if the performance data does not satisfy the selected component-specific criteria and wherein said network performance data includes end-to-end latency across all connected network components, said end to end latency being directly measured by said measuring step along the actual data path taken between any connected network components over said network and without requiring intermediate or remote monitoring devices or endpoints, and h. displaying an alarm response selected from the group consisting of the first response and the second response, wherein the alarm response is displayed on a monitor of the central monitoring station and the affected patient monitor, based on a determination that the waveform data is adversely affected, wherein other connected network components are not affected.

2. The system as recited in claim 1, further comprising the step of displaying a second alarm on the first network component, wherein the second alarm corresponds to the alarm response.

3. The system as recited in claim 2, further comprising an access point disposed between the central monitoring station and the first network component.

4. The system as recited in claim 1, wherein the selected component-specific criteria includes a hold-off delay period such that the performance data must satisfy the selected component-specific criteria for the hold-off delay period for the alarm condition to change state.

5. The system as recited in claim 1, wherein the selected component-specific criteria includes hysteresis.

6. The system as recited in claim 1, further comprising the step of recording the performance data, thus producing recorded performance data.

7. The system as recited in claim 6, wherein the recorded performance data is extracted and analyzed.

8. The system as recited in claim 7, further comprising the step of monitoring a trend in the stored performance data for the first network component as a function of time.

9. The system as recited in claim 1, wherein the performance data is selected from the group consisting of number of retries, signal strength data, packet loss data, latency data and combinations thereof.

10. The system as recited in claim 1, further comprising the step of determining a degree to which each of the network components from the plurality of network components deviates from their corresponding component-specific criteria.

11. The system as recited in claim 10, further comprising the step of displaying a list that includes network components ordered by the degree to which the network components deviate from their corresponding component-specific criteria.

12. The system as recited in claim 11, wherein only those network components which fail to satisfy their corresponding component-specific criteria are listed.

13. The system as recited in claim 1, further comprising the step of requesting the performance data from the first network component.

14. The system as recited in claim 1, further comprising the step of evaluating the performance data for the first network component and determining baseline values for the performance data.

15. The system as recited in claim 1, wherein the performance data is selected from the group consisting of jitter, bandwidth, quality of service tags, number of clients, packets transmission and reception counts, byte transmission and reception counts, errors, and combinations thereof.

* * * * *